United States Patent [19]
Chien

[11] Patent Number: 5,214,956
[45] Date of Patent: Jun. 1, 1993

[54] METHOD AND APPARATUS FOR DETERMINING STEAM QUALITY BY MEASURING THE CONDENSATE RATE OF A STEAM SAMPLE FLOWING THROUGH A CRITICAL FLOW NOZZLE

[76] Inventor: Sze-Foo Chien, P.O. Box 770070, Houston, Tex. 77215-0070

[21] Appl. No.: 597,122

[22] Filed: Oct. 15, 1990

[51] Int. Cl.⁵ .................... G01N 25/60; G01F 1/36
[52] U.S. Cl. ................................................ 73/29.01
[58] Field of Search ............... 73/29.01, 29.03, 861.04

[56] References Cited

U.S. PATENT DOCUMENTS

| | | | |
|---|---|---|---|
| 4,576,036 | 3/1986 | Huang et al. | 73/29.01 |
| 4,576,043 | 3/1986 | Nguyen | 73/29.01 |
| 4,836,032 | 6/1989 | Redus et al. | 73/861.04 |
| 5,031,465 | 7/1991 | Redus | 73/861.04 |
| 5,031,466 | 7/1991 | Redus | 73/861.04 |

*Primary Examiner*—Hezron E. Williams
*Assistant Examiner*—Joseph W. Roskos

[57] ABSTRACT

Steam quality is determined by taking a sample of the steam and measuring the steam pressure and the rate of condensate of the sampled steam.

7 Claims, 3 Drawing Sheets

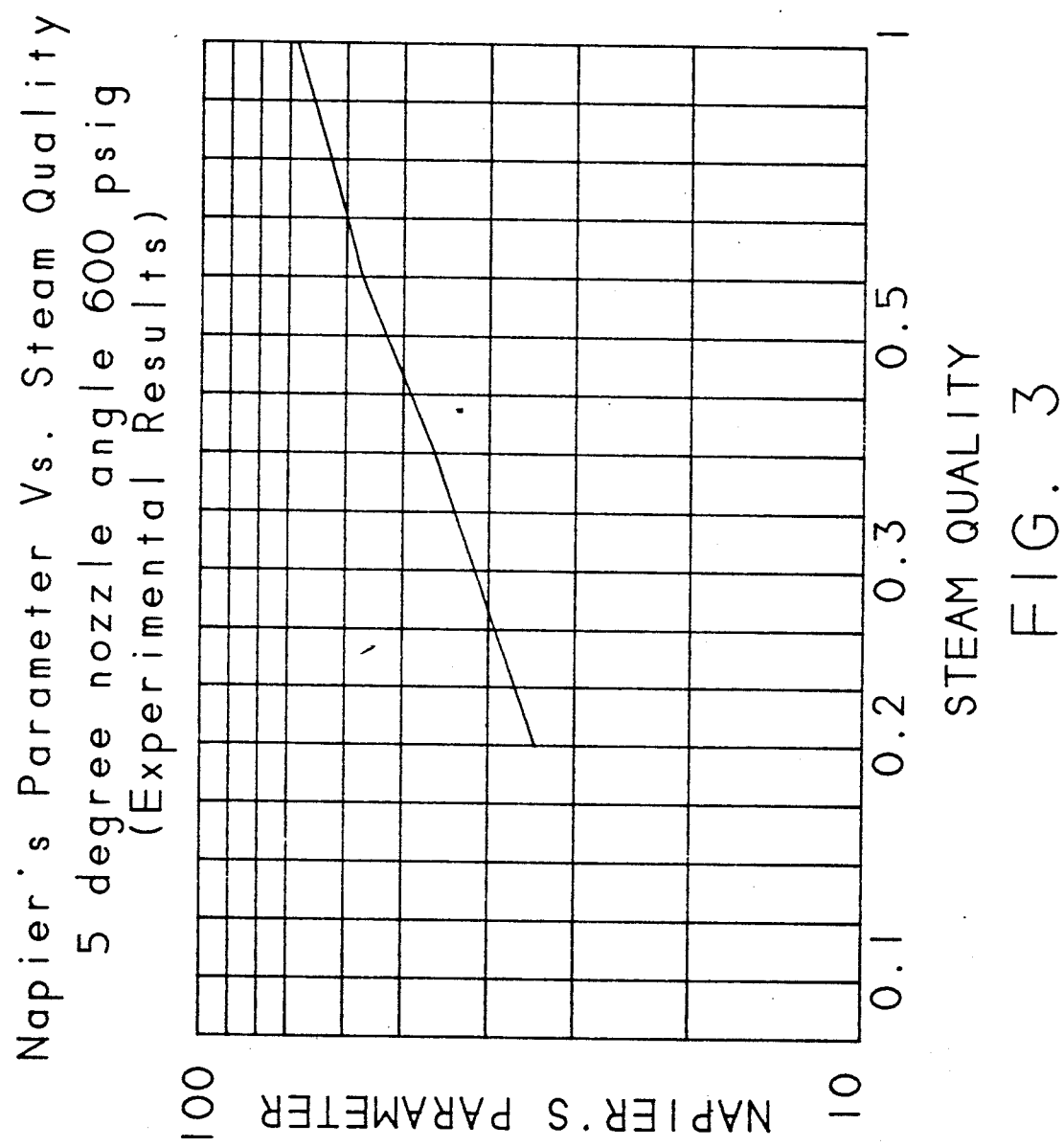

METHOD AND APPARATUS FOR DETERMINING STEAM QUALITY BY MEASURING THE CONDENSATE RATE OF A STEAM SAMPLE FLOWING THROUGH A CRITICAL FLOW NOZZLE

BACKGROUND OF THE INVENTION

1. The Field of Invention

The present invention relates to a method and apparatus for determining steam quality only by sampling the steam and passing the sampled steam through a critical flow nozzle, measuring pressure upstream of the nozzle, condensing the sampled steam and then measuring the condensate rate.

2. The Prior Art

Steam flooding has become an accepted practice for recovery of petroleum products from marginal fields or reservoirs that require a degree of stimulation to produce a satisfactory flow of crude petroleum. There is a need for a simple method and apparatus to determine the quality of steam at the wellhead of an injection well. Such a measurement, if simplified, would be particularly useful in determining the amount of heat which is applied to the underground reservoir by the injected steam.

The measurement or monitoring of steam quality is important since the steam's quality and thereby its reservoir or formation heatup effect directly affects the resulting production operations. Further, the quality of the steam which can be most economically injected into a particular substrate or reservoir is contingent on a number of circumstances. The latter include the age of the reservoir and the anticipated prospects for extracting commercially justified amounts of hydrocarbon products therefrom.

In brief, it is desirable that the quality of steam which is injected into each injection well be altered or adjusted to a level of quality that best conforms to the condition of the formation penetrated by that well. Clearly the quality of the steam must be known before any alteration or adjustment can be made.

It is known that in order to be particularly effective in this type of stimulation operation, the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source and the effectiveness of pipe insulation. It will further depend on the pipe layout including number and orientation of fittings through which the steam has to travel prior to reaching the injection port or well because of phase separation that can occur in these fittings.

It is important, therefore, as a matter of economic practicality that a flow monitoring and controlling means be instituted into the steam-carrying conduit immediately upstream of each injection wellhead.

Prior art to measure the steam quality by a throttle calorimeter is limited to steam of very high quality (for quality greater than 93%). However, oil-field steam which is generally produced in a single-pass steam generator which produces steam at a quality less than 85% cannot use a throttle calorimeter to determine its quality.

SUMMARY OF THE INVENTION

The present invention utilizes the static pressure immediately upstream of a nozzle and the flow rate through the nozzle to determine the quality of this steam. The flow through the nozzle has to be in a "critical flow" condition and the discharge from the nozzle is condensed, by any appropriate means, and the condensate rate is measured. Steam quality is determined from this measurement.

BRIEF DESCRIPTION OF THE DRAWING

The present invention will be described by way of example with reference to the accompanying drawings in which:

FIG. 3 is a plot of Napier's Parameter vs. Steam Quality based on experimental results.

DETAILED DESCRIPTION OF THE PREFERRED EMBODIMENT

Figure 1:
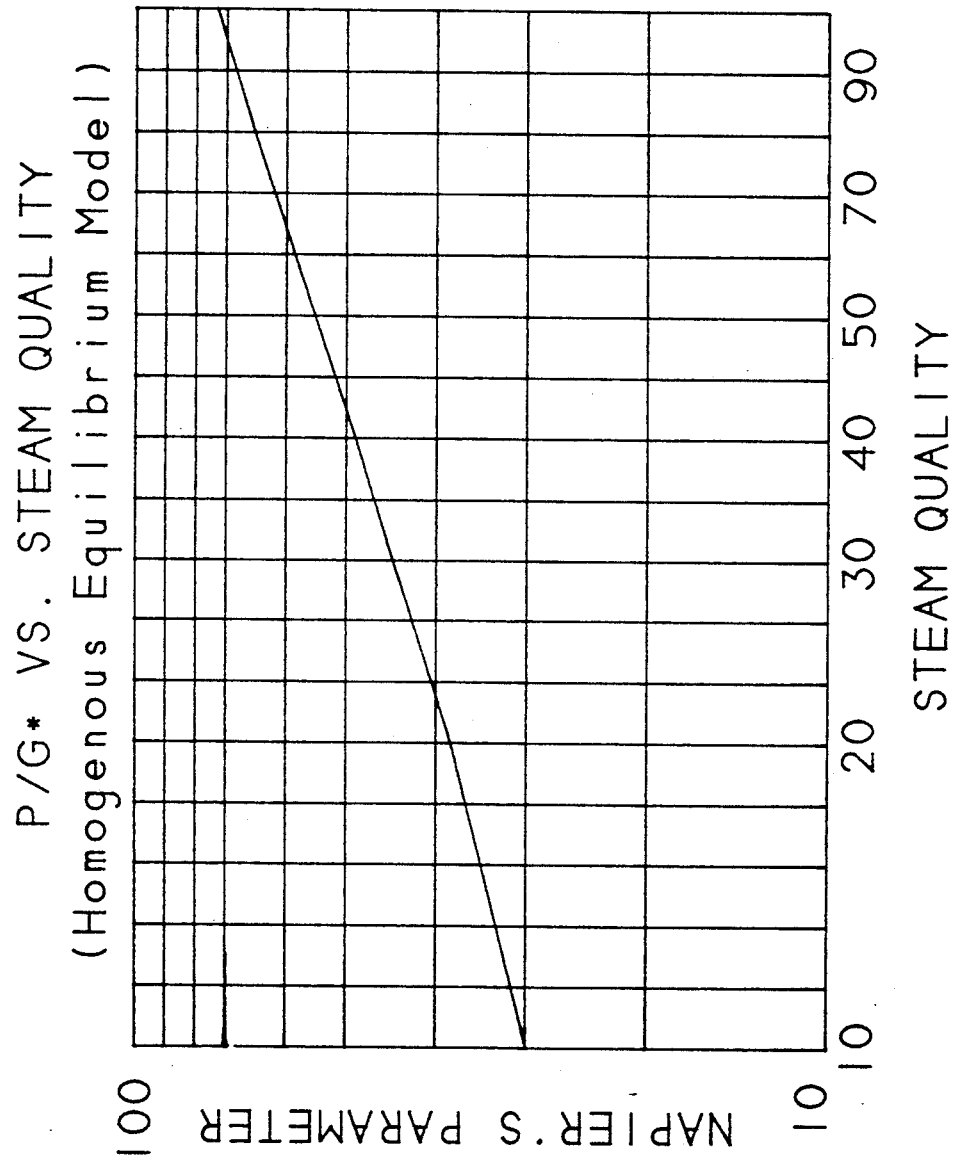
FIG. 1 is a plot of $P^o/G^*$ vs Steam Quality based on analytical data of Homogenous Equilibrium Model.

The analytical results of the critical flow of nozzle using Homogenous Equilibrium Model showed that the parameter $P^o/G^*$ is a unique function of steam quality and that it is almost independent of the steam pressure. The $P^o$ is the steam pressure (in psia) upstream of a nozzle and $G^*$ (in $lb_m/in^2$-s) is the critical mass flux through the nozzle. The value of $P^o/G^*$ is in the neighborhood of 30 for 10% quality steam and increases to approximately 70 for 100% quality steam. A plot of $P^o/G^*$ for steam at 211 psia and 646 psia is shown in FIG. 1. The variation of this parameter with respect to steam quality led to the discovery of the subject inventive method for measuring the steam quality. Namely, by measuring pressure upstream from a nozzle and by measuring the condensate rate of a steam sample flowing under critical condition through a nozzle one can determine the steam quality X, $$\left[ \text{i.e. } X = X\left(\frac{P^o}{G^*}\right) \right].$$

Experimental values of $P^o/G^*$ versus quality are shown in FIG. 3 which shows that the correlations between $P^o/G^*$ and steam quality can be easily established.

Figure 2:
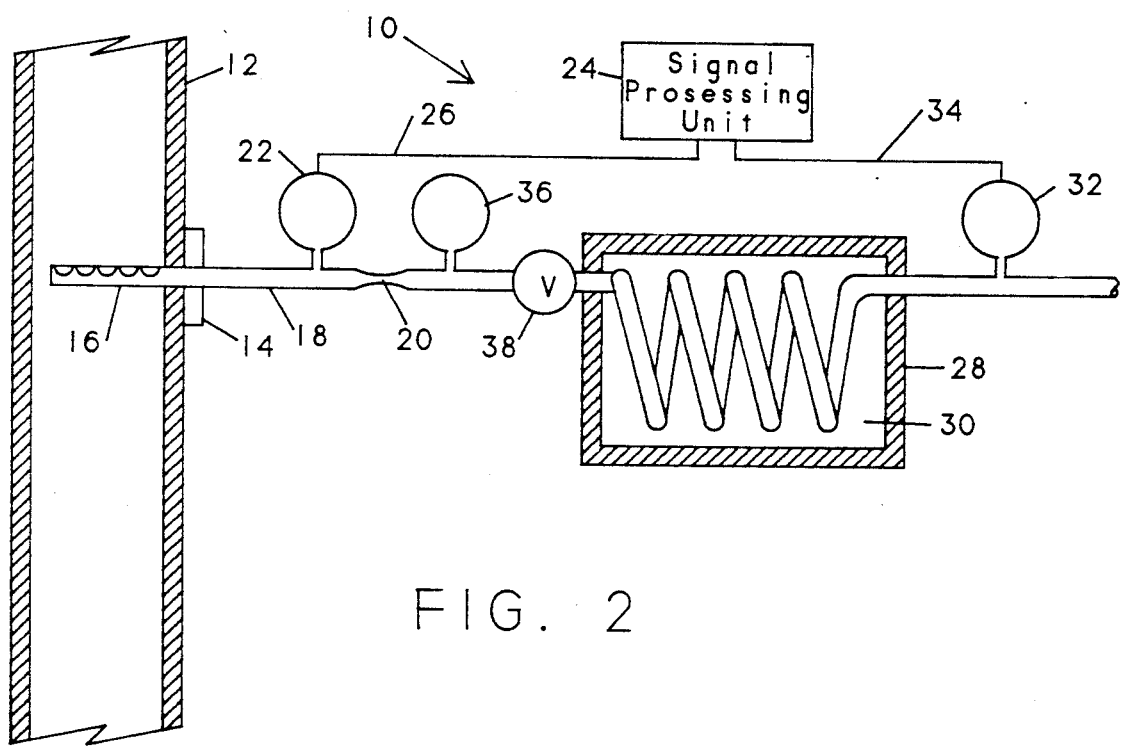
FIG. 2 is a schematic diagram of an apparatus for performing the present invention.

An apparatus 10 for performing the measurements of the present invention is shown schematically in FIG. 2. The steam line 12 is assumed to be of sufficiently large diameter that it would be inconvenient, if not impractical, to permanently mount any measuring means therein. The line 12 is therefor provided with a tap 14 of known configuration which allows insertion of a sampling probe 16 into the steam flow line 12. The sampling probe 16 is directly connected to conduit 18 which has a small nozzle 20 therein. The pressure in conduit 18 upstream of the nozzle 20 is measured by gauge 22 and this information transmitted to a signal processing unit 24 via conductor 26. Steam discharge from nozzle 20 is condensed in a known condensing unit 28 using a standard coolant 30. Meter means 32 measure the output flow rate of the condensed steam either by its weight (or volume) and time or by flow. The flow rate information is transmitted to the signal processing unit 24 via conductor 34. The signal processing unit 24 calculates steam quality according to P°/G*. Pressure downstream of the nozzle 20 is measured by gauge 36 to assure the flow through the nozzle is at critical flow. To assure critical flow through the nozzle, the pressure downstream of the nozzle should be equal to or less than one-half of the pressure upstream of the nozzle. This can be accomplished by adjustable valve means 38 on the downstream side of nozzle 22.

The nozzle 20 in this measuring system preferably has a fairly small throat in order to reduce the cooling requirement for the condensing unit 28. A nozzle throat diameter of 1/16" to ⅛" will be appropriate for most steam flow conditions.

The approximate condensate rate (or critical flow rate) has been estimated as follows:

| Nozzle throat diameter | Condensate Flow Rate at 600 psia | |
|---|---|---|
| inches | 10% Quality | 100% Quality |
| 0.1 | 9.42 lb$_m$/min. | 4.04 lb$_m$/min |
| 0.0625(1/16) | 3.68 lb$_m$/min. | 1.58 lb$_m$/min |

The condensate rate is directly proportional to the steam pressure. The choice of the size of nozzle 20 and condensing unit 28 are determined according to steam pressure and the rated capacity of the condensing unit.

The present invention may be subject to many modifications and changes without departing from the spirit or essential characteristics thereof. The present embodiment is therefor intended in all respects to be illustrative and not restrictive as to the scope of the invention as defined by the appended claims.

I claim:

1. A method for determining the quality of steam flowing in a steam system, comprising the steps of:
    sampling steam flowing in said system and sending said sample through a nozzle at critical flow condition;
    measuring pressure upstream of said nozzle;
    passing discharge from said nozzle through a condensing unit; and
    measuring the rate of condensation whereby the quality of said steam is determined from said measurements.

2. A method according to claim 1 wherein said flow rate is measured by weight and time.

3. A method according to claim 1 wherein said flow rate is measured by volume and time.

4. A method according to claim 1 further comprising the step of:
    measuring steam pressure downstream of the nozzle to determine that the flow through the nozzle is at critical flow.

5. A method according to claim 1 wherein the value of P°/G* is calculated and the steam quality is determined from the relationship between P°/G* and the steam quality, wherein P° is the steam pressure upstream of the nozzle and G* is the critical mass flux through the nozzle.

6. a device to determine quality of steam flowing in a steam system comprising:
    probe means adapted to be inserted in a steam line and sample steam at that point in the system;
    conduit means connected to receive sampled steam from aid probe means;
    nozzle means within said conduit means;
    means in said conduit means to measure steam pressure upstream of said nozzle means;
    means connected to said conduit means to condense the sampled steam downstream of said nozzle means; and
    means to measure the rate of condensation whereby the quality of the sampled steam is determined according to the ratio of steam pressure to the steam flux through the throat of the nozzle means, and a predetermined relationship between steam quality and the volume of the steam pressure to steam flux ratio.

7. The device according to claim 6 further comprising:
    means to measure pressure in said conduit means downstream of said nozzle means whereby operation at critical flow is determined.

* * * * *

UNITED STATES PATENT AND TRADEMARK OFFICE
CERTIFICATE OF CORRECTION

PATENT NO. : 5,214,956

DATED : June 1, 1993

INVENTOR(S) : Sze-Foo Chien

It is certified that error appears in the above-identified patent and that said Letters Patent is hereby corrected as shown below:

ON THE TITLE PAGE:

(73) Assignee: Texaco Inc., White Plains, NY

Signed and Sealed this

Twenty-fifth Day of January, 1994

Attest:

BRUCE LEHMAN

Attesting Officer　　　Commissioner of Patents and Trademarks